US006468296B1

(12) United States Patent
Dobak, III et al.

(10) Patent No.: US 6,468,296 B1
(45) Date of Patent: Oct. 22, 2002

(54) METHOD FOR LOW TEMPERATURE THROMBOLYSIS AND LOW TEMPERATURE THROMBOLYTIC AGENT WITH SELECTIVE ORGAN TEMPERATURE CONTROL

(75) Inventors: John D. Dobak, III, La Jolla, CA (US); Juan C. Lasheras, La Jolla, CA (US)

(73) Assignee: Innercool Therapies, Inc., San Diego, CA (US)

( * ) Notice: Subject to any disclaimer, the term of this patent is extended or adjusted under 35 U.S.C. 154(b) by 0 days.

(21) Appl. No.: 09/714,749

(22) Filed: Nov. 16, 2000

Related U.S. Application Data

(60) Division of application No. 09/215,039, filed on Dec. 16, 1998, now Pat. No. 6,251,129, which is a continuation-in-part of application No. 09/052,545, filed on Mar. 31, 1998, now Pat. No. 6,231,595, which is a continuation-in-part of application No. 09/103,342, filed on Jun. 23, 1998, now Pat. No. 6,096,068, which is a continuation-in-part of application No. 09/047,012, filed on Mar. 24, 1998, now Pat. No. 5,957,963, which is a continuation-in-part of application No. 09/012,287, filed on Jan. 23, 1998, now Pat. No. 6,051,019.

(51) Int. Cl.[7] .................................................. A61F 7/00
(52) U.S. Cl. ........................ 607/105; 607/106; 607/113; 606/21; 128/898
(58) Field of Search .......................... 607/96, 105, 106, 607/113; 606/20, 21, 22, 23, 24, 25, 26; 128/898

(56) References Cited

U.S. PATENT DOCUMENTS

| | | | | |
|---|---|---|---|---|
| 2,308,484 A | * | 1/1943 | Auzin et al. | |
| 2,374,609 A | * | 4/1945 | McCollum | |
| 2,615,686 A | * | 10/1952 | Davidson | |
| 2,672,032 A | * | 3/1954 | Towse | |
| 2,913,009 A | * | 11/1959 | Kuthe | |
| 3,298,371 A | * | 1/1967 | Lee | |
| 3,425,419 A | * | 2/1969 | Dato | |
| 3,504,674 A | * | 4/1970 | Swenson et al. | |
| 3,865,116 A | * | 2/1975 | Brooks | |
| 3,888,259 A | * | 6/1975 | Miley | |

(List continued on next page.)

FOREIGN PATENT DOCUMENTS

| | | |
|---|---|---|
| EP | 0655225 A1 | 5/1993 |
| EP | 0 664 990 | 11/1997 |

(List continued on next page.)

OTHER PUBLICATIONS

Yenari; *Thrombolysis with Tissue Plasminogen Activator (TPA) is Temperature Dependent*; July 1994; pp. 475–481; Thrombosis Research, vol. 77, No. 5.

(List continued on next page.)

*Primary Examiner*—Rosiland S. Kearney
(74) *Attorney, Agent, or Firm*—Mark D. Wieczorek

(57) ABSTRACT

The invention provides a method for substantially reducing the size of a thrombus in a blood vessel in which blood is flowing. The method includes delivering a heat transfer element to a blood vessel in fluid communication with a thrombosed blood vessel. The temperature of the heat transfer element is adjusted such that the same is sufficient to remove heat from the flowing blood. Heat is transferred from a volume including the thrombus to the heat transfer element. In a separate embodiment, heat may be delivered to the volume including the thrombus from the heat transfer element. The resultant temperature of the volume may be sufficient to substantially reduce the size of a thrombus. For example, the resultant temperature of the volume may be sufficiently high to substantially enhance plasminogen activation near the thrombus. In a separate embodiment, a therapeutic drug may be delivered to the blood vessel to further reduce the size of a thrombus, the drug having an optimal temperature at the hypothermic or hyperthermic temperature of the blood.

5 Claims, 6 Drawing Sheets

U.S. PATENT DOCUMENTS

| | | | |
|---|---|---|---|
| 3,971,383 A | * | 7/1976 | Van Gerven |
| 4,038,519 A | * | 7/1977 | Foucras |
| 4,153,048 A | * | 5/1979 | Magrini |
| 4,190,033 A | * | 2/1980 | Foti |
| 4,231,425 A | * | 11/1980 | Engstrom |
| 4,275,734 A | * | 6/1981 | Mitchiner |
| 4,298,006 A | * | 11/1981 | Parks |
| 4,318,722 A | * | 3/1982 | Altman |
| 4,427,009 A | * | 1/1984 | Wells et al. |
| 4,445,500 A | * | 5/1984 | Osterholm |
| 4,483,341 A | * | 11/1984 | Witteles |
| 4,502,286 A | * | 3/1985 | Okada et al. |
| 4,569,355 A | * | 2/1986 | Bitterly |
| 4,581,017 A | * | 4/1986 | Sahota |
| 4,655,746 A | * | 4/1987 | Daniels et al. |
| 4,672,962 A | * | 6/1987 | Hershenson |
| 4,748,979 A | * | 6/1988 | Hershenson |
| 4,750,493 A | * | 6/1988 | Brader |
| 4,762,129 A | * | 8/1988 | Bonzel |
| 4,820,349 A | * | 4/1989 | Saab |
| 4,860,744 A | * | 8/1989 | Johnson et al. |
| 4,883,455 A | * | 11/1989 | Leonard |
| 4,894,164 A | | 1/1990 | Polaschegg |
| 4,904,237 A | | 2/1990 | Janese |
| 4,920,963 A | | 5/1990 | Brader |
| 4,964,409 A | | 10/1990 | Tremulis |
| 5,002,531 A | | 3/1991 | Bonzel |
| 5,014,695 A | | 5/1991 | Benak et al. |
| 5,018,521 A | | 5/1991 | Campbell |
| 5,019,075 A | | 5/1991 | Spears et al. |
| 5,041,089 A | | 8/1991 | Mueller et al. |
| 5,078,713 A | | 1/1992 | Varney |
| 5,092,841 A | | 3/1992 | Spears |
| 5,106,360 A | | 4/1992 | Ishwara et al. |
| 5,108,390 A | | 4/1992 | Potocky et al. |
| 5,110,721 A | | 5/1992 | Anaise et al. |
| 5,117,822 A | | 6/1992 | Laghi |
| 5,147,355 A | | 9/1992 | Friedman et al. |
| 5,149,321 A | | 9/1992 | Klatz et al. |
| 5,150,706 A | | 9/1992 | Cox et al. |
| 5,151,100 A | | 9/1992 | Abele et al. |
| 5,190,539 A | | 3/1993 | Fletcher et al. |
| 5,191,883 A | | 3/1993 | Lennox et al. |
| 5,196,024 A | | 3/1993 | Barath |
| 5,211,631 A | | 5/1993 | Sheaff |
| 5,234,405 A | | 8/1993 | Klatz et al. |
| 5,246,421 A | | 9/1993 | Saab |
| 5,248,312 A | | 9/1993 | Langberg |
| 5,250,070 A | | 10/1993 | Parodi |
| 5,257,977 A | | 11/1993 | Eshel |
| 5,264,260 A | | 11/1993 | Saab |
| 5,267,341 A | | 11/1993 | Shearin |
| 5,269,369 A | | 12/1993 | Faghri |
| 5,269,749 A | | 12/1993 | Koturov |
| 5,269,758 A | | 12/1993 | Taheri |
| 5,281,213 A | | 1/1994 | Milder et al. |
| 5,281,215 A | | 1/1994 | Milder |
| 5,306,261 A | | 4/1994 | Alliger et al. |
| 5,310,440 A | | 5/1994 | Zingher |
| 5,334,193 A | | 8/1994 | Nardella |
| 5,342,301 A | | 8/1994 | Saab |
| 5,342,621 A | | 8/1994 | Eury |
| 5,344,436 A | | 9/1994 | Fontenot et al. |
| 5,358,486 A | | 10/1994 | Saab |
| 5,365,750 A | | 11/1994 | Greenthal |
| 5,368,591 A | | 11/1994 | Lennox et al. |
| 5,383,918 A | | 1/1995 | Panetta |
| 5,395,314 A | | 3/1995 | Klatz et al. |
| 5,395,331 A | | 3/1995 | O'Neill et al. |
| 5,403,281 A | | 4/1995 | O'Neill et al. |
| 5,417,686 A | | 5/1995 | Peterson et al. |
| 5,423,745 A | | 6/1995 | Todd et al. |
| 5,423,807 A | | 6/1995 | Milder |
| 5,433,740 A | | 7/1995 | Yamaguchi |
| 5,437,673 A | | 8/1995 | Baust et al. |
| 5,443,456 A | | 8/1995 | Alliger et al. |
| 5,462,521 A | | 10/1995 | Brucker et al. |
| 5,486,204 A | | 1/1996 | Clifton |
| 5,486,208 A | | 1/1996 | Ginsburg |
| 5,499,973 A | | 3/1996 | Saab |
| 5,531,776 A | | 7/1996 | Ward et al. |
| 5,558,644 A | | 9/1996 | Boyd et al. |
| 5,569,195 A | | 10/1996 | Saab |
| 5,573,532 A | | 11/1996 | Chang et al. |
| 5,584,804 A | | 12/1996 | Klatz et al. |
| 5,588,438 A | | 12/1996 | McKown et al. |
| 5,591,162 A | | 1/1997 | Fletcher et al. |
| 5,620,480 A | | 4/1997 | Rudie |
| 5,624,392 A | | 4/1997 | Saab |
| 5,643,197 A | | 7/1997 | Brucker et al. |
| 5,647,051 A | | 7/1997 | Neer |
| 5,676,693 A | | 10/1997 | Lafontaine |
| 5,709,654 A | | 1/1998 | Klatz |
| 5,713,941 A | | 2/1998 | Robins et al. |
| 5,716,386 A | | 2/1998 | Ward et al. |
| 5,735,809 A | | 4/1998 | Gorsuch |
| 5,797,878 A | | 8/1998 | Bleam |
| 5,800,480 A | | 9/1998 | Augustine et al. |
| 5,807,391 A | | 9/1998 | Wijkamp |
| 5,824,030 A | | 10/1998 | Yang et al. |
| 5,827,222 A | | 10/1998 | Klatz et al. |
| 5,827,237 A | | 10/1998 | Macoviak et al. |
| 5,833,671 A | | 11/1998 | Macoviak et al. |
| 5,837,003 A | | 11/1998 | Ginsburg |
| 5,861,021 A | | 1/1999 | Thome et al. |
| 5,871,526 A | | 2/1999 | Gibbs et al. |
| 5,873,835 A | | 2/1999 | Hastings et al. |
| 5,879,329 A | | 3/1999 | Ginsburg |
| 5,899,899 A | | 5/1999 | Arless et al. |
| 5,902,268 A | | 5/1999 | Saab |
| 5,913,885 A | | 6/1999 | Klatz et al. |
| 5,913,886 A | | 6/1999 | Soloman |
| 5,916,242 A | | 6/1999 | Schwartz |
| 5,957,963 A | | 9/1999 | Dobak |
| 5,989,238 A | | 11/1999 | Ginsburg |
| 6,019,783 A | | 2/2000 | Philips et al. |
| 6,022,336 A | | 2/2000 | Zadno-Azizi et al. |
| 6,033,383 A | | 3/2000 | Ginsburg |
| 6,042,559 A | | 3/2000 | Dobak, III |
| 6,110,168 A | | 3/2000 | Ginsburg |
| 6,051,019 A | | 4/2000 | Dobak, III |
| 6,126,684 A | | 10/2000 | Gobin et al. |
| 6,146,411 A | | 11/2000 | Noda et al. |
| 6,149,670 A | | 11/2000 | Worthen et al. |
| 6,149,673 A | | 11/2000 | Ginsburg |
| 6,149,676 A | | 11/2000 | Ginsburg |

FOREIGN PATENT DOCUMENTS

| | | |
|---|---|---|
| FR | 2 447 406 | 3/1980 |
| SU | 806 029 | 2/1981 |
| WO | WO 91/05528 | 5/1991 |
| WO | WO 93/04727 | 3/1993 |
| WO | WO 95/01814 | 1/1995 |
| WO | WO 96/40347 | 12/1996 |
| WO | WO 97/01374 | 1/1997 |
| WO | WO 97/25011 | 7/1997 |
| WO | WO 98/26831 | 6/1998 |
| WO | WO 98/31312 | 7/1998 |
| WO | WO 98/49957 | 11/1998 |
| WO | WO 99/02096 | 1/1999 |
| WO | WO 99/37226 | 7/1999 |

| | | |
|---|---|---|
| WO | WO 99/44519 | 9/1999 |
| WO | WO 99/48449 | 9/1999 |
| WO | WO 99/56812 | 11/1999 |
| WO | WO 99/66970 | 12/1999 |
| WO | WO 99/66971 | 12/1999 |
| WO | WO 00/09054 | 2/2000 |
| WO | WO 00/10494 | 3/2000 |
| WO | WO 00/38601 | 7/2000 |
| WO | WO 00/47145 | 8/2000 |
| WO | WO 00/48670 | 8/2000 |
| WO | WO 00/51534 | 9/2000 |
| WO | WO 00/53135 | 9/2000 |
| WO | WO 00/57823 | 10/2000 |
| WO | WO 00/66053 | 11/2000 |
| WO | WO 00/72779 | 12/2000 |

OTHER PUBLICATIONS

Yoshihara; *Changes in Coagulation and Fibrinolysis Occurring in Dogs during Hypothermia*; Aug. 1984; pp. 503–512; Thrombosis Research, vol. 37, No. 4.

Zarins; *Circulation in Profound Hypothermia*; Nov. 1972; pp. 97–104; Journal of Surgical Research, vol. 14, N.2.

Parkins; *Brain Cooling in the Prevention of Brain Damage During Periods of Circulatory Occlusion in Dogs*; Apr. 1954; pp. 284–289; Annals of Surgery, vol. 140, No. 3.

Piepgras; *Rapid Active Internal Core Cooling for Induction of Moderate Hypothermia in Head Injury by Use of an Extracorporeal Heat Exchanger*; Feb. 1998; pp. 311–318; Neurosurgery, vol. 42, No. 2.

Rijken; *Plasminogen Activation at Low Temperatures in Plasma Samples Containing Therapeutic Concentrations of Tissue–Type Plasminogen Activator or Other Thrombolytic Agents*; Oct. 1989; pp. 47–52; place of publication unknown.

Rohrer, M. J. and A. M. Natale (1992), "Effect of Hypothermia on the Coagulation Cascade," *Critical Care Medicine*, 20:1402–1405, Oct.

Schwartz, A. E. et al.; (1996); *Isolated cerebral hypothermia by single carotid artery perfusion of extracorporeally cooled blood in baboons*; Neurosurgery 39(3):577–582.

Schwartz; *Cerebral Blood Flow during Low–flow Hypothermic Cardiopulmonary Bypass in Baboons*; Jun. 1994; pp. 959–964; Anesthesiology, vol. 81, No. 4

Schwartz: *Selective Cerebral Hypothermia by Means of Transfemoral Internal Carotid Artery Catheterization*; May 1996; pp. 571–572; Radiology, vol. 201, No. 2.

Schmid–Elsaesser, R. et al. (1999), "Combination Drug Therapy and Mild Hypothermia: A Promising Treatmet Strategy for Reversible, Focal Cerebral Ischemia," *Stroke*, 30:1891–1899.

Steen; *The Detrimental Effects of Prolonged Hypothermia and Rewarming in the Dog*; Aug. 1979 ;pp. 224–230; Anesthesiology, vol. 52, No. 3.

Vandam; *Hypothermia*; Sep. 1959; pp. 546–553; The New England Journal of Medicine.

White; *Cerebral Hypothermia and Circulatory Arrest*; Jul. 1978; pp. 450–458; Mayo Clinic Proceedings, vol. 53.

Jos R.C. Jansen, Ph.D., et al. (1997) *Near continuous cardiac output by thermodilution*. Journal of Clinical Monitoring 13:233–239.

Kimoto; *Open Heart Surgery Under Direct Vision with the Aid of Brain–Cooling by Irrigation*; Jul. 1955; pp. 592–603; Surgery, vol. 39, No. 4.

Kurz, M. et al. (1993), "Naloxone, Meperidine, and Shivering," *Anesthesiology* 79;1193–1201.

Leslie, K. et al. (1994), "Propofol Causes a Dose–Dependent Decrease in the Thermoregulatory Threshold for Vasoconstriction but has Little Effect on Sweating," *Anesthesiology* 81:353–360.

Marekovic, Z.; *Abstract of Renal Hypothermia in Situ by Venous Passages: Experimental Work on Dogs*; 1980; Eur Urol 6(2); 1 page.

Matsukawa, T. et al. (1995), "Propofol Linearly Reduces the Vasoconstriction and Shivering Thresholds," *Anesthesiology*, 82 (5):1169–1180, May.

Meden; *Effect of Hypothermia and Delayed Thrombolysis in a Rat Embolic Stroke Model*; Dec. 1993; pp. 91–98; Acta Neurologica Scandinavica.

Meden; *The Influence of Body Temperature on Infarct Volume and Thrombolytic Therapy in a Rat Embolic Stoke Model*; Feb. 1994; pp. 131–138; Brain Research, vol. 647.

Milleret, Rene; *La cryo–chirurgie danes les varices des mimbres inferieurs*; Angiologie; Supplement au no. 110.

Milleret; Abstract of *Cryosclerosis of the Saphenous Veins in Varicose Reflux in the Obese and Elderly*; Oct. 1981; one page; Phlebologie, vol. 34, No. 4.

Overgaard et al. *Effect of Hypothermia and Delayed Thrombolysis in a Rat Embolic Stroke Model*, Acta Neural, No. 90/1994, 91–94.

Ambrus; *The Biphasic Nature and Temperature Dependence of the Activation of Human Plasminogen by Urokinase*; May 1979; pp. 339–347; Research Communications in Chemical Pathology and Pharmacology, vol. 24, No. 2.

Buggy, D. et al. (1997), "Clonidine at Induction Reduces Shivering After General Anaesthesia," *Can. J. Anaesth.* 44 (3):263–267.

Bigelo: *Hypothermia, Its Possible Role in Cardiac Surgery*; Nov. 1959; pp. 849–866; Annals of Surgery, vol. 132, No. 5.

Cheatle; *Cryostripping the Long and Short Saphenous Veins*; Jan. 1993; one page; Br. J. Surg., vol. 80.

Dexter; *Blood Warms as It Blows Retrograde from a Femoral Cannulation Site to the Carotid Artery During Cardiopulmonary Bypass*; Nov. 1994; pp. 393–397; Perfusion, vol. 9, No. 6.

Giesbrecht, G. G. et al. (1997), "Inhibition of Shivering Increases Core Temperature Afterdrop and Attenuates Rewarming in Hypothermic Humans," *American Physiological Society*, 0161–7567: 1630–1634.

Gillinov; *Superior Cerebral Protection with Profound Hypothermia During Circulatory Arrest*; Nov. 1992, pp. 1432–1439; Ann. Thorac. Surg., vol. 55.

Higazi; The Effect of Ultrasonic Irradiation and Temperature on Fibrinolytic Activity in Vitro; Aug. 1992; pp. 251–253; Thrombosis Research, vol. 69, No. 2.

Imamaki; *Retrograde Cerebral Perfusion with Hypothermic Blood Provides Efficient Protection of the Brain*; Jul. 1995; pp. 325–333; Journal of Cardiac Surgery, vol. 10, No. 4, Part 1.

Jolin; *Management of a Giant Intracranial Aneurysm Using Surface–Heparinized Extracorporeal Circulation and Controlled Deep Hypothermic Low Flow Perfusion*; Aug. 1992; pp. 756–760; Acta Anaesthesiologica Scandinavia.

* cited by examiner

METHOD FOR LOW TEMPERATURE THROMBOLYSIS AND LOW TEMPERATURE THROMBOLYTIC AGENT WITH SELECTIVE ORGAN TEMPERATURE CONTROL

CROSS REFERENCE TO RELATED APPLICATIONS

This is a divisional of U.S. patent application Ser. No. 09/215,039, filed on Dec. 16, 1998, U.S. Pat. No. 6,251,129 and entitled "Method for Low Temperature Thrombolysis and Low Temperature Thrombolytic Agent with Selective Organ Temperature Control", which is a continuation-in-part patent application of U.S. patent application Ser. No. 09/103,342, filed on Jun. 23, 1998, and entitled "Selective Organ Cooling Catheter and Method of Using the Same", now issued as U.S. Pat. No. 6,096,068 on Aug. 1, 2000; U.S. patent application Ser. No. 09/047,012, filed on Mar. 24, 1998, and entitled "Selective Organ Hypothermia Method and Apparatus", now issued as U.S. Pat. No. 5,957,963 on Sep. 28, 1999; and U.S. patent application Ser. No. 09/052,545, filed on Mar. 31, 1998, U.S. Pat. No. 6,231,595 and entitled "Circulating Fluid Hypothermia Method and Apparatus"; the latter of which is a continuation-in-part patent application of U.S. patent application Ser. No. 09/012,287, filed on Jan. 23, 1998, and entitled "Selective Organ Hypothermia Method and Apparatus", now issued as U.S. Pat. No. 6,051,019 on Apr. 18, 2000.

STATEMENT REGARDING FEDERALLY SPONSORED RESEARCH OR DEVELOPMENT

Not Applicable

BACKGROUND OF THE INVENTION

Field of the Invention—The present invention relates generally to the modification and control of optimal temperatures for enzymes. More particularly, the invention relates to the modification and control of optimal temperatures for enzymes for use in treatments such as thrombolysis.

Background Information—Organs in the human body, such as the brain, kidney and heart, are maintained at a constant temperature of approximately 37° C. Hypothermia can be clinically defined as a core body temperature of 35° C. or less. Hypothermia is sometimes characterized further according to its severity. A body core temperature in the range of 33° C. to 35° C. is described as mild hypothermia. A body temperature of 28° C. to 32° C. is described as moderate hypothermia. A body core temperature in the range of 24° C. to 28° C. is described as severe hypothermia.

Hypothermia is uniquely effective in reducing brain injury caused by a variety of neurological insults and may eventually play an important role in emergency brain resuscitation. Experimental evidence has demonstrated that cerebral cooling improves outcome after global ischemia, focal ischemia, or traumatic brain injury. For this reason, hypothermia may be induced in order to reduce the effect of certain bodily injuries to the brain as well as other organs.

Cerebral hypothermia has traditionally been accomplished through whole body cooling to create a condition of total body hypothermia in the range of 20° C. to 30° C. However, the use of total body hypothermia risks certain deleterious systematic vascular effects. For example, total body hypothermia may cause severe derangement of the cardiovascular system, including low cardiac output, elevated systematic resistance, and ventricular fibrillation. Other side effects include renal failure, disseminated intravascular coagulation, and electrolyte disturbances. In addition to the undesirable side effects, total body hypothermia is difficult to administer.

Catheters have been developed which are inserted into the bloodstream of the patient in order to induce total body hypothermia. For example, U.S. Pat. No. 3,425,419 to Dato describes a method and apparatus of lowering and raising the temperature of the human body. Dato induces moderate hypothermia in a patient using a metallic catheter. The metallic catheter has an inner passageway through which a fluid, such as water, can be circulated. The catheter is inserted through the femoral vein and then through the inferior vena cava as far as the right atrium and the superior vena cava. The Dato catheter has an elongated cylindrical shape and is constructed from stainless steel. By way of example, Dato suggests the use of a catheter approximately 70 cm in length and approximately 6 mm in diameter. However, use of the Dato device implicates the negative effects of total body hypothermia described above.

Due to the problems associated with total body hypothermia, attempts have been made to provide more selective cooling. For example, cooling helmets or head gear have been used in an attempt to cool only the head rather than the patient's entire body. However, such methods rely on conductive heat transfer through the skull and into the brain. One drawback of using conductive heat transfer is that the process of reducing the temperature of the brain is prolonged. Also, it is difficult to precisely control the temperature of the brain when using conduction due to the temperature gradient that must be established externally in order to sufficiently lower the internal temperature. In addition, when using conduction to cool the brain, the face of the patient is also subjected to severe hypothermia, increasing discomfort and the likelihood of negative side effects. It is known that profound cooling of the face can cause similar cardiovascular side effects as total body cooling. From a practical standpoint, such devices are cumbersome and may make continued treatment of the patient difficult or impossible.

Selected organ hypothermia has been accomplished using extracorporeal perfusion, as detailed by Arthur E. Schwartz, M.D. et al., in *Isolated Cerebral Hypothermia by Single Carotid Artery Perfusion of Extracorporeally Cooled Blood in Baboons,* which appeared in Vol. 39, No. 3, NEUROSURGERY 577 (September, 1996). In this study, blood was continually withdrawn from baboons through the femoral artery. The blood was cooled by a water bath and then infused through a common carotid artery with its external branches occluded. Using this method, normal heart rhythm, systemic arterial blood pressure and arterial blood gas values were maintained during the hypothermia. This study showed that the brain could be selectively cooled to temperatures of 20° C. without reducing the temperature of the entire body. However, external circulation of blood is not a practical approach for treating humans because the risk of infection, need for anticoagulation, and risk of bleeding is too great. Further, this method requires cannulation of two vessels making it more cumbersome to perform particularly in emergency settings. Even more, percutaneous cannulation of the carotid artery is difficult and potentially fatal due to the associated arterial wall trauma. Finally, this method would be ineffective to cool other organs, such as the kidneys, because the feeding arteries cannot be directly cannulated percutaneously.

Selective organ hypothermia has also been attempted by perfusion of a cold solution such as saline or perflourocarbons. This process is commonly used to protect the heart during heart surgery and is referred to as cardioplegia. Perfusion of a cold solution has a number of drawbacks, including a limited time of administration due to excessive volume accumulation, cost, and inconvenience of maintaining the perfusate and lack of effectiveness due to the temperature dilution from the blood. Temperature dilution by the blood is a particular problem in high blood flow organs such as the brain.

Selective organ hypothermia is useful in limiting brain injury after ischemia or traumatic brain injury, as noted above. For example, neurons subjected to ischemia may die. Selective cooling of these neurons, such as by nerve cooling, has been shown to increase the survival rate. Hypothermic temperatures which may be employed include, e.g., 20° C. to 35° C.

Ischemia is blockage of the arteries that supply blood to a tissue. The blockage itself is referred to as a clot or thrombus and results from the solidification of fibrinogen into fibrin. A stroke is ischemia where the arteries to the brain are blocked. In a stroke, the clot forms in the cerebral or pre-cerebral arteries. This type of blockage may also be caused by a thrombus that breaks free from the heart and flows into an artery through which it cannot pass. In other words, the thrombus gets lodged in the artery.

Clots can be treated in several ways. One way, fibrinolysis, employs enzymes that lyse, or break up and dissolve, the clot. Thrombolysis is fibrinolysis used to treat thrombosed vessels. The enzymes that lyse clots are termed thrombolytics because thrombin is the enzyme that coagulates fibrinogen. Streptokinase("SK"), urokinase ("UK"), and tissue plasminogen activator ("tPA") are thrombolytics and are often used in this capacity. These enzymes can be given as drugs by intravenous injection or by intraarterial delivery using a catheter with a fluid outlet port near or at the site of the clot.

Drug administration is occasionally problematic as some sensitive patients encounter adverse reactions to drugs. Moreover, there is a risk of hemorrhage when these drugs are given intravenously. There is a need for a method of lysing clots that does not rely solely or partially on drug administration. There is further a need for a method of lysing clots in which the effects of ischemia on affected cells is minimized.

In some cases, of course, the extent or nature of the clot indicates that drug therapies must be used. The effectiveness of drug therapies is dependent on several factors, including the temperature of the environment in which the drug acts. Thus, there is further a need for a drug therapy which is effective to treat a thrombus and which is also complementary to efforts to reduce ischemia, especially when those efforts employ hypothermia.

BRIEF SUMMARY OF THE INVENTION

In one aspect, the invention relates to a method for substantially reducing the size of a thrombus in a blood vessel. The method includes delivering a heat transfer element to a blood vessel in fluid communication with a thrombosed blood vessel. The temperature of the heat transfer element is adjusted such that the same is sufficient to remove heat from the flowing blood. Heat is transferred from a volume of blood including the thrombus to the heat transfer element. The resultant temperature of the volume may be sufficient to substantially reduce the size of a thrombus. For example, the resultant temperature of the volume may be sufficiently high to substantially enhance plasminogen activation near the thrombus.

Implementations of the invention may include one or more of the following. The temperature of the blood may be adjusted by the heat transfer element to a temperature of between about 30° C. and 32° C. The temperature sufficient to substantially reduce the size of a thrombus is also sufficient to substantially reduce plasmin inhibitor activity near the thrombus. The temperature of the heat transfer element may be raised from a temperature sufficient to substantially reduce the size of the thrombus to a temperature sufficient to substantially rewarm the volume, and may further be cycled between these temperatures. In this case, the temperature sufficient to reduce the size of the thrombus is between about 25° C. and 32° C., and the temperature sufficient to substantially rewarm the volume is between about 34° C. and 36° C.

The delivering and adjusting may further include inserting the heat transfer element into the vessel and cooling the heat transfer element by delivering a working fluid to the heat transfer element. The working fluid may be delivered at a temperature of between about −3° C. and 1° C. The heat transfer element may be inflated with the working fluid, which may be delivered at a pressure of less than 5 atmospheres, such as about 1 to 5 atmospheres.

Turbulence may also be induced in the flowing blood or in the working fluid. Regarding the former, turbulence may be induced with a turbulence intensity of greater than about 0.05. Blood turbulence may be induced in greater than 20% of the period of the cardiac cycle within the carotid artery, such as during the entire period of the cardiac cycle. To induce turbulence in the working fluid, the inflating may include passing the working fluid through a substantially helical-shaped structure. About 75 to 200 watts of heat may be removed from the blood.

In another aspect, the invention relates to a method for dissolving a blood clot. The method includes introducing a catheter having a cooling element into a blood vessel in which a blood clot has formed and disposing the cooling element within the blood vessel such that blood flows past the cooling element to the blood clot. At least a portion of the volume of blood surrounding the blood clot is cooled. Free stream turbulence may be induced in blood flowing over the catheter. The method thus reduces inhibition of anti-clotting enzymes by the cooling.

In yet another aspect, the invention relates to a method of altering the activity of an enzyme present in a flow of blood relative to the activity of the enzyme at a normal blood temperature. The method includes delivering a heat transfer element to the blood flow upstream of the enzyme, adjusting the temperature of the heat transfer element such that the temperature of the heat transfer element is sufficient to alter the temperature of a local portion of the blood flow including the enzyme, and transferring heat between the portion of the blood flow and the heat transfer element. The resultant temperature of the portion of the blood flow is sufficient to substantially alter the enzyme activity within at least the portion of the blood flow.

Implementations of the invention may include extending the technique to stationary volumes of blood or tissue. The adjusting may further include cooling the heat transfer element by delivering a working fluid to the heat transfer element and inducing turbulence within the working fluid or in the flow of blood.

In a further aspect, the invention is related to a method for providing an optimal working temperature for a temperature-specific enzyme with a drug in a blood vessel. The method includes delivering a heat transfer element to a blood vessel, the blood vessel containing a temperature-specific enzyme. The temperature of the heat transfer element is adjusted such that the temperature-specific enzyme is heated to a prespecified temperature range within at least a portion of which the optimal working temperature for a temperature-specific enzyme is attained. The optimal working temperature in the blood vessel is substantially different from the normal body temperature in the blood vessel.

In another aspect, the invention is directed towards a method for selective thrombolysis by selective vessel hypothermia. The method includes introducing a catheter having a heat transfer element into a blood vessel in fluid communication with a thrombosed blood vessel. The heat transfer element is cooled by flowing a working fluid through the heat transfer element. The blood is cooled by flowing the blood past the heat transfer element and inducing free stream turbulence in the blood, such that the blood is cooled to a prespecified temperature range. A thrombolytic drug is then delivered to the blood, the thrombolytic drug having a working temperature within the prespecified temperature range.

Implementations of the invention may include one or more of the following. The drug may be chosen from tPA, urokinase, streptokinase, precursors of urokinase, and combinations thereof. If the drug is tPA, the prespecified temperature range may be between about 30° C. to 32° C. The blood may then be rewarmed and cycled. If the thrombolytic drug is streptokinase, the prespecified temperature range may between about 30° C. and 32° C., and the rewarming may raise the blood temperature to about 37° C. If the thrombolytic drug is urokinase, the prespecified temperature range may be below about 28° C., and the rewarming may raise the blood temperature to about 37° C. If the thrombolytic drug is a precursor to urokinase, the prespecified temperature range may be below about 28° C., and the rewarming may raise the blood temperature to about 37° C.

In yet another aspect, the blood may be warmed instead of cooled. In this case, if the drug is tPA, the prespecified temperature range may be between about 37° C. to 40° C.

Advantages of the invention include one or more of the following. Clot lysis may be achieved conveniently and selectively, and may be induced without the need for additional anticoagulants. The effects of ischemia are reduced during the procedure, reducing damage to affected cells. In the case where drugs are administered to further treat a thrombus, hypothermia may also be induced as a complementary therapy to reduce the effects of ischemia and to provide neural protection.

The novel features of this invention, as well as the invention itself, will be best understood from the attached drawings, taken along with the following description, in which similar reference characters refer to similar parts, and in which:

DETAILED DESCRIPTION OF THE INVENTION

Figure 1:
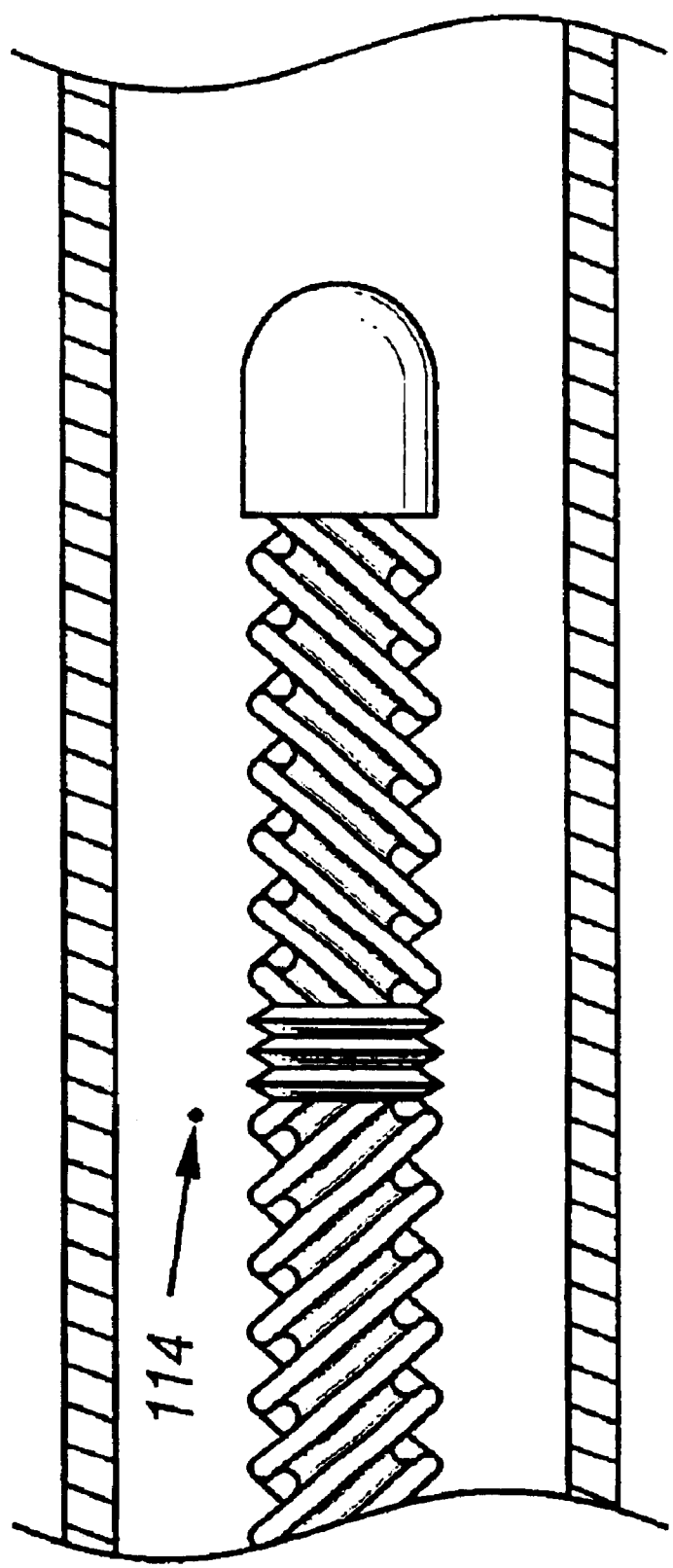
FIG. 1 is an elevation view of a turbulence inducing heat transfer element within an artery.

The temperature of a selected organ may be intravascularly regulated by a heat transfer element placed in the organ's feeding artery to absorb or deliver heat to or from the blood flowing into the organ. While the method is described with respect to blood flow into an organ, it is understood that heat transfer within a volume of tissue is analogous. In the latter case, heat transfer is predominantly by conduction.

The heat transfer may cause either a cooling or a heating of the selected organ. A heat transfer element that selectively alters the temperature of an organ should be capable of providing the necessary heat transfer rate to produce the desired cooling or heating effect within the organ to achieve a desired temperature.

The heat transfer element should be small and flexible enough to fit within the feeding artery while still allowing a sufficient blood flow to reach the organ in order to avoid ischemic organ damage. Feeding arteries, like the carotid artery, branch off the aorta at various levels. Subsidiary arteries continue to branch off these initial branches. For example, the internal carotid artery branches off the common carotid artery near the angle of the jaw. The heat transfer element is typically inserted into a peripheral artery, such as the femoral artery, using a guide catheter or guide wire, and accesses a feeding artery by initially passing though a series of one or more of these branches. Thus, the flexibility and size, e.g., the diameter, of the heat transfer element are important characteristics. This flexibility is achieved as is described in more detail below.

These points are illustrated using brain cooling as an example. The common carotid artery supplies blood to the head and brain. The internal carotid artery branches off the common carotid artery to supply blood to the anterior cerebrum. The heat transfer element may be placed into the common carotid artery or into both the common carotid artery and the internal carotid artery.

The benefits of hypothermia described above are achieved when the temperature of the blood flowing to the brain is reduced to between 30° C. and 32° C. A typical brain has a blood flow rate through each carotid artery (right and left) of approximately 250–375 cubic centimeters per minute (cc/min). With this flow rate, calculations show that the heat transfer element should absorb approximately 75–175 watts of heat when placed in one of the carotid arteries to induce the desired cooling effect. Smaller organs may have less blood flow in their respective supply arteries and may require less heat transfer, such as about 25 watts.

The method employs conductive and convective heat transfers. Once the materials for the device and a working fluid are chosen, the conductive heat transfers are solely dependent on the temperature gradients. Convective heat transfers, by contrast, also rely on the movement of fluid to transfer heat. Forced convection results when the heat transfer surface is in contact with a fluid whose motion is induced (or forced) by a pressure gradient, area variation, or other such force. In the case of arterial flow, the beating heart provides an oscillatory pressure gradient to force the motion of the blood in contact with the heat transfer surface. One of the aspects of the device uses turbulence to enhance this forced convective heat transfer.

The rate of convective heat transfer Q is proportional to the product of S, the area of the heat transfer element in direct contact with the fluid, $\Delta T = T_b - T_s$, the temperature differential between the surface temperature $T_s$ of the heat transfer element and the free stream blood temperature $T_b$, and $\overline{h}_c$, the average convection heat transfer coefficient over the heat transfer area. $\overline{h}_c$ is sometimes called the "surface coefficient of heat transfer" or the "convection heat transfer coefficient".

The magnitude of the heat transfer rate Q to or from the fluid flow can be increased through manipulation of the above three parameters. Practical constraints limit the value of these parameters and how much they can be manipulated. For example, the internal diameter of the common carotid artery ranges from 6 to 8 mm. Thus, the heat transfer element residing therein may not be much larger than 4 mm in diameter to avoid occluding the vessel. The length of the heat transfer element should also be limited. For placement within the internal and common carotid artery, the length of the heat transfer element is limited to about 10 cm. This estimate is based on the length of the common carotid artery, which ranges from 8 to 12 cm.

Consequently, the value of the surface area S is limited by the physical constraints imposed by the size of the artery into which the device is placed. Surface features, such as fins, can be used to increase the surface area of the heat transfer element, however, these features alone cannot provide enough surface area enhancement to meet the required heat transfer rate to effectively cool the brain.

One may also attempt to vary the magnitude of the heat transfer rate by varying $\Delta T$. The value of $\Delta T = T_b - T_s$ can be varied by varying the surface temperature $T_s$ of the heat transfer element. The allowable surface temperature of the heat transfer element is limited by the characteristics of blood. The blood temperature is fixed at about 37° C., and blood freezes at approximately 0° C. When the blood approaches freezing, ice emboli may form in the blood which may lodge downstream, causing serious ischemic injury. Furthermore, reducing the temperature of the blood also increases its viscosity which results in a small decrease in the value of $\overline{h}_c$. Increased viscosity of the blood may further result in an increase in the pressure drop within the artery, thus compromising the flow of blood to the brain. Given the above constraints, it is advantageous to limit the surface temperature of the heat transfer element to approximately 1° C.–5° C., thus resulting in a maximum temperature differential between the blood stream and the heat transfer element of approximately 32° C.–36° C.

One may also attempt to vary the magnitude of the heat transfer rate by varying $\overline{h}_c$. Fewer constraints are imposed on the value of the convection heat transfer coefficient $\overline{h}_c$. The mechanisms by which the value of $\overline{h}_c$ may be increased are complex. However, one way to increase $\overline{h}_c$ for a fixed mean value of the velocity is to increase the level of turbulent kinetic energy in the fluid flow.

The heat transfer rate $Q_{no-flow}$ in the absence of fluid flow is proportional to $\Delta T$, the temperature differential between the surface temperature $T_s$ of the heat transfer element and the free stream blood temperature $T_b$ times k, the diffusion constant, and is inversely proportion to $\delta$, the thickness of the boundary layer.

The magnitude of the enhancement in heat transfer by fluid flow can be estimated by taking the ratio of the heat transfer rate with fluid flow to the heat transfer rate in the absence of fluid flow $N = Q_{flow}/Q_{no-flow} = \overline{h}_c/(k/\delta)$. This ratio is called the Nusselt number ("Nu"). For convective heat transfer between blood and the surface of the heat transfer element, Nusselt numbers of 30–80 have been found to be appropriate for selective cooling applications of various organs in the human body. Nusselt numbers are generally dependent on several other numbers: the Reynolds number, the Womersley number, and the Prandtl number.

Stirring-type mechanisms, which abruptly change the direction of velocity vectors, may be utilized to induce turbulent kinetic energy and increase the heat transfer rate. The level of turbulence so created is characterized by the turbulence intensity $\vartheta$. Turbulence intensity $\vartheta$ is defined as the root mean square of the fluctuating velocity divided by the mean velocity. Such mechanisms can create high levels of turbulence intensity in the free stream, thereby increasing the heat transfer rate. This turbulence intensity should ideally be sustained for a significant portion of the cardiac cycle, and should ideally be created throughout the free stream and not just in the boundary layer.

Turbulence does occur for a short period in the cardiac cycle anyway. In particular, the blood flow is turbulent during a small portion of the descending systolic flow. This portion is less than 20% of the period of the cardiac cycle. If a heat transfer element is placed co-axially inside the artery, the heat transfer rate will be enhanced during this short interval. For typical of these fluctuations, the turbulence intensity is at least 0.05. In other words, the instantaneous velocity fluctuations deviate from the mean velocity by at least 5%. Although ideally turbulence is created throughout the entire period of the cardiac cycle, the benefits of turbulence are obtained if the turbulence is sustained for 75%, 50% or even as low as 30% or 20% of the cardiac cycle.

One type of turbulence-inducing heat transfer element which may be advantageously employed to provide heating or cooling of an organ or volume is described in co-pending U.S. patent application Ser. No. 09/103,342 to Dobak and Lasheras for a "Selective Organ Cooling Catheter and Method of Using the Same," incorporated by reference above. In that application, and as described below, the heat transfer element is made of a high thermal conductivity material, such as metal. The use of a highly thermally conductive material increases the heat transfer rate for a given temperature differential between the coolant within the heat transfer element and the blood. This facilitates the use of a higher temperature coolant within the heat transfer element, allowing safer coolants, such as water, to be used. Highly thermally conductive materials, such as metals, tend to be rigid. In that application, bellows provided a high degree of articulation that compensated for the intrinsic stiffness of the metal. The device size was minimized, e.g., less than 4 mm, to prevent blockage of the blood flowing in the artery. Therefore, the design of the heat transfer element should facilitate flexibility in an inherently inflexible material.

To create the desired level of turbulence intensity in the blood free stream during the whole cardiac cycle, one embodiment of the device uses a modular design. This design creates helical blood flow and produces a high level of turbulence in the free stream by periodically forcing abrupt changes in the direction of the helical blood flow. FIG. 1 is a perspective view of such a turbulence inducing heat transfer element within an artery. Turbulent flow would be found at point 114, in the free stream area. The abrupt changes in flow direction are achieved through the use of a series of two or more heat transfer segments, each comprised of one or more helical ridges. To affect the free stream, the depth of the helical ridge is larger than the thickness of the boundary layer which would develop if the heat transfer element had a smooth cylindrical surface.

The use of periodic abrupt changes in the helical direction of the blood flow in order to induce strong free stream turbulence may be illustrated with reference to a common clothes washing machine. The rotor of a washing machine spins initially in one direction causing laminar flow. When the rotor abruptly reverses direction, significant turbulent kinetic energy is created within the entire wash basin as the changing currents cause random turbulent motion within the clothes-water slurry.

Figure 2:
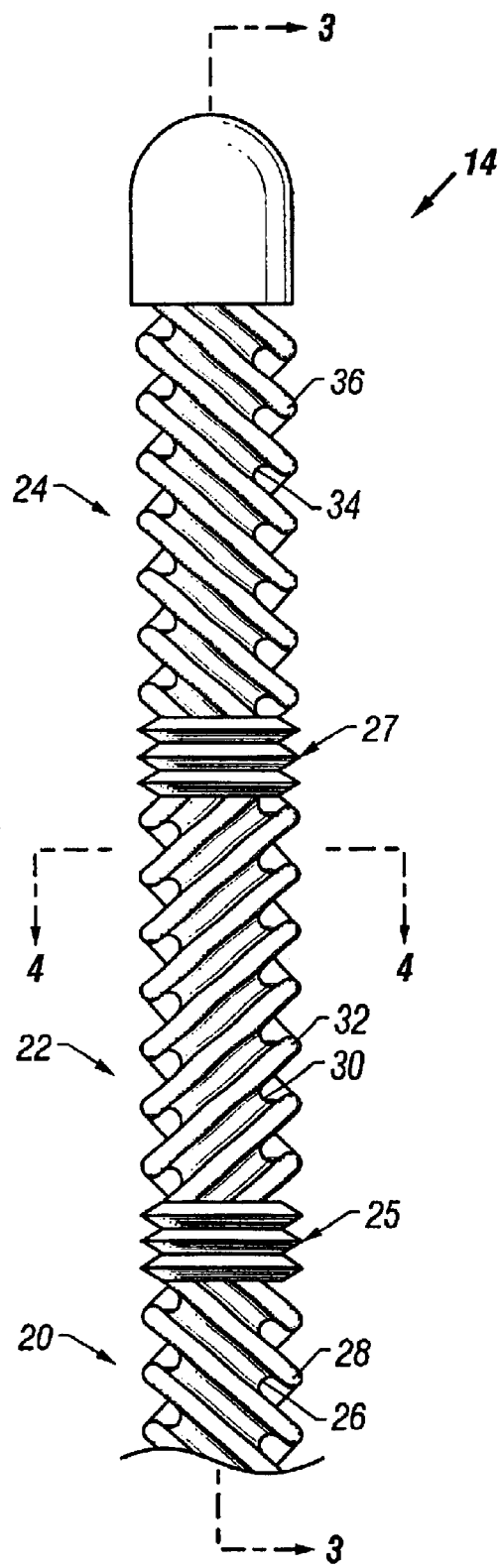
FIG. 2 is an elevation view of one embodiment of a heat transfer element which may be employed according to the invention.

FIG. 2 is an elevation view of one embodiment of a heat transfer element 14. The heat transfer element 14 is comprised of a series of elongated, articulated segments or modules 20, 22, 24. Three such segments are shown in this embodiment, but two or more such segments could be used. As seen in FIG. 2, a first elongated heat transfer segment 20 is located at the proximal end of the heat transfer element 14. A turbulence-inducing exterior surface of the segment 20 comprises four parallel helical ridges 28 with four parallel helical grooves 26 therebetween. One, two, three, or more parallel helical ridges 28 could also be used. In this embodiment, the helical ridges 28 and the helical grooves 26 of the heat transfer segment 20 have a left hand twist, referred to herein as a counter-clockwise spiral or helical rotation, as they proceed toward the distal end of the heat transfer segment 20.

The first heat transfer segment 20 is coupled to a second elongated heat transfer segment 22 by a first bellows section 25, which provides flexibility and compressibility. The second heat transfer segment 22 comprises one or more helical ridges 32 with one or more helical grooves 30 therebetween. The ridges 32 and grooves 30 have a right hand, or clockwise, twist as they proceed toward the distal end of the heat transfer segment 22. The second heat transfer segment 22 is coupled to a third elongated heat transfer segment 24 by a second bellows section 27. The third heat transfer segment 24 comprises one or more helical ridges 36 with one or more helical grooves 34 therebetween. The helical ridge 36 and the helical groove 34 have a left hand, or counter-clockwise, twist as they proceed toward the distal end of the heat transfer segment 24. Thus, successive heat transfer segments 20, 22, 24 of the heat transfer element 14 alternate between having clockwise and counterclockwise helical twists. The actual left or right hand twist of any particular segment is immaterial, as long as adjacent segments have opposite helical twist.

In addition, the rounded contours of the ridges 28, 32, 36 also allow the heat transfer element 14 to maintain a relatively atraumatic profile, thereby minimizing the possibility of damage to the blood vessel wall. A heat transfer element may be comprised of two, three, or more heat transfer segments.

The bellows sections 25, 27 are formed from seamless and nonporous materials, such as metal, and therefore are impermeable to gas, which can be particularly important, depending on the type of working fluid which is cycled through the heat transfer element 14. The structure of the bellows sections 25, 27 allows them to bend, extend and compress, which increases the flexibility of the heat transfer element 14 so that it is more readily able to navigate through blood vessels. The bellows sections 25, 27 also provide for axial compression of the heat transfer element 14, which can limit the trauma when the distal end of the heat transfer element 14 abuts a blood vessel wall. The bellows sections 25, 27 are also able to tolerate cryogenic temperatures without a loss of performance.

The exterior surfaces of the heat transfer element 14 can be made from metal, and may comprise very high thermal conductivity materials such as nickel, thereby facilitating heat transfer. Alternatively, other metals such as stainless steel, titanium, aluminum, silver, copper and the like, can be used, with or without an appropriate coating or treatment to enhance biocompatibility or inhibit clot formation. Suitable biocompatible coatings include, e.g., gold, platinum or polymer paralyene. The heat transfer element 14 may be manufactured by plating a thin layer of metal on a mandrel that has the appropriate pattern. In this way, the heat transfer element 14 may be manufactured inexpensively in large quantities, which is an important feature in a disposable medical device.

Because the heat transfer element 14 may dwell within the blood vessel for extended periods of time, such as 24–48 hours or even longer, it may be desirable to treat the surfaces of the heat transfer element 14 to avoid clot formation. In particular, one may wish to treat the bellows sections 25, 27 because stagnation of the blood flow may occur in the convolutions, thus allowing clots to form and cling to the surface to form a thrombus. One means by which to prevent thrombus formation is to bind an antithrombogenic agent to the surface of the heat transfer element 14. For example, heparin is known to inhibit clot formation and is also known to be useful as a biocoating. Alternatively, the surfaces of the heat transfer element 14 may be bombarded with ions such as nitrogen. Bombardment with nitrogen can harden and smooth the surface and, thus prevent adherence of clotting factors to the surface.

Figure 3:
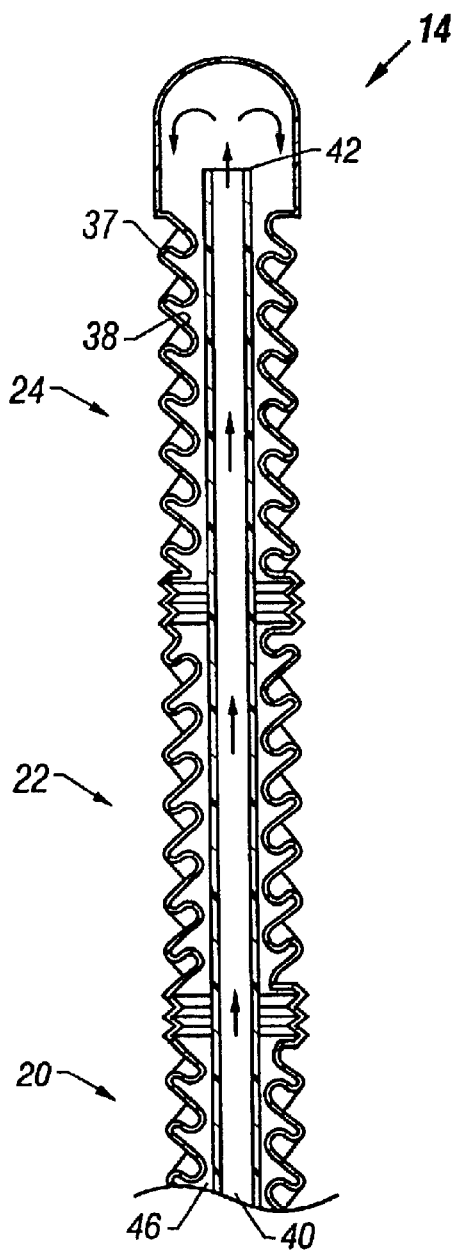
FIG. 3 is longitudinal section view of the heat transfer element of FIG. 2.

FIG. 3 is a longitudinal sectional view of the heat transfer element 14, taken along line 3—3 in FIG. 2. Some interior contours are omitted for purposes of clarity. An inner tube 42 creates an inner coaxial lumen 42 and an outer coaxial lumen 46 within the heat transfer element 14. Once the heat transfer element 14 is in place in the blood vessel, a working fluid such as saline or other aqueous solution may be circulated through the heat transfer element 14. Fluid flows up a supply catheter into the inner coaxial lumen 40. At the distal end of the heat transfer element 14, the working fluid exits the inner coaxial lumen 40 and enters the outer lumen 46. As the working fluid flows through the outer lumen 46, heat is transferred from the working fluid to the exterior surface 37 of the heat transfer element 14. Because the heat transfer element 14 is constructed from a high conductivity material, the temperature of its exterior surface 37 may reach very close to the temperature of the working fluid. The tube 42 may be formed as an insulating divider to thermally separate the inner lumen 40 from the outer lumen 46. For example, insulation may be achieved by creating longitudinal air channels in the wall of the insulating tube 42. Alternatively, the insulating tube 42 may be constructed of a non-thermally conductive material like polytetrafluoroethylene or some other polymer.

It is important to note that the same mechanisms that govern the heat transfer rate between the exterior surface 37 of the heat transfer element 14 and the blood also govern the heat transfer rate between the working fluid and the interior surface 38 of the heat transfer element 14. The heat transfer characteristics of the interior surface 38 are particularly important when using water, saline or other fluid which remains a liquid as the coolant. Other coolants such as freon undergo nucleate boiling and create turbulence through a different mechanism. Saline is a safe coolant because it is non-toxic, arid leakage of saline does not result in a gas embolism, which could occur with the use of boiling refrigerants. Since turbulence in the coolant is enhanced by the shape of the interior surface 38 of the heat transfer element 14, the coolant can be delivered to the heat transfer element 14 at a warmer temperature and still achieve the necessary heat transfer rate.

This has a number of beneficial implications in the need for insulation along the catheter shaft length. Due to the decreased need for insulation, the catheter shaft diameter can be made smaller. The enhanced heat transfer characteristics of the interior surface of the heat transfer element 14 also allow the working fluid to be delivered to the heat transfer element 14 at lower flow rates and lower pressures. High pressures may make the heat transfer element stiff and cause it to push against the wall of the blood vessel, thereby shielding part of the exterior surface 37 of the heat transfer element 14 from the blood. Because of the increased heat transfer characteristics achieved by the alternating helical ridges 28, 32, 36, the pressure of the working fluid may be as low as 5 atmospheres, 3 atmospheres, 2 atmospheres or even less than 1 atmosphere.

Figure 4:
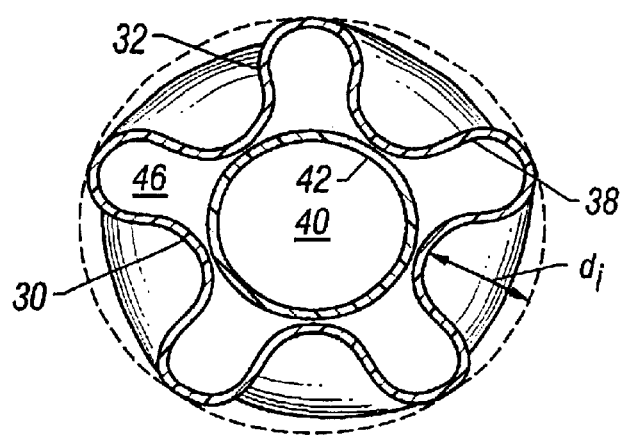
FIG. 4 is a transverse section view of the heat transfer element of FIG. 2.

FIG. 4 is a transverse sectional view of the heat transfer element 14, taken at a location denoted by the line 4—4 in FIG. 2. FIG. 4 illustrates a five lobed embodiment, whereas FIG. 2 illustrates a four-lobed embodiment. As mentioned earlier, any number of lobes might be used. In FIG. 4, the coaxial construction of the heat transfer element 14 is clearly shown. The inner coaxial lumen 40 is defined by the insulating coaxial tube 42. The outer lumen 46 is defined by the exterior surface of the insulating coaxial tube 42 and the interior surface 38 of the heat transfer element 14. In addition, the helical ridges 32 and helical grooves 30 may be seen in FIG. 4. As noted above, in the preferred embodiment, the depth of the grooves, $d_i$, is greater than the boundary layer thickness which would have developed if a cylindrical heat transfer element were introduced. For example, in a heat transfer element 14 with a 4 mm outer diameter, the depth of the invaginations, $d_i$, may be approximately equal to 1 mm if designed for use in the carotid artery. Although FIG. 4 shows four ridges and four grooves, the number of ridges and grooves may vary. Thus, heat transfer elements with 1, 2, 3, 4, 5, 6, 7, 8 or more ridges are specifically contemplated.

Figure 5:
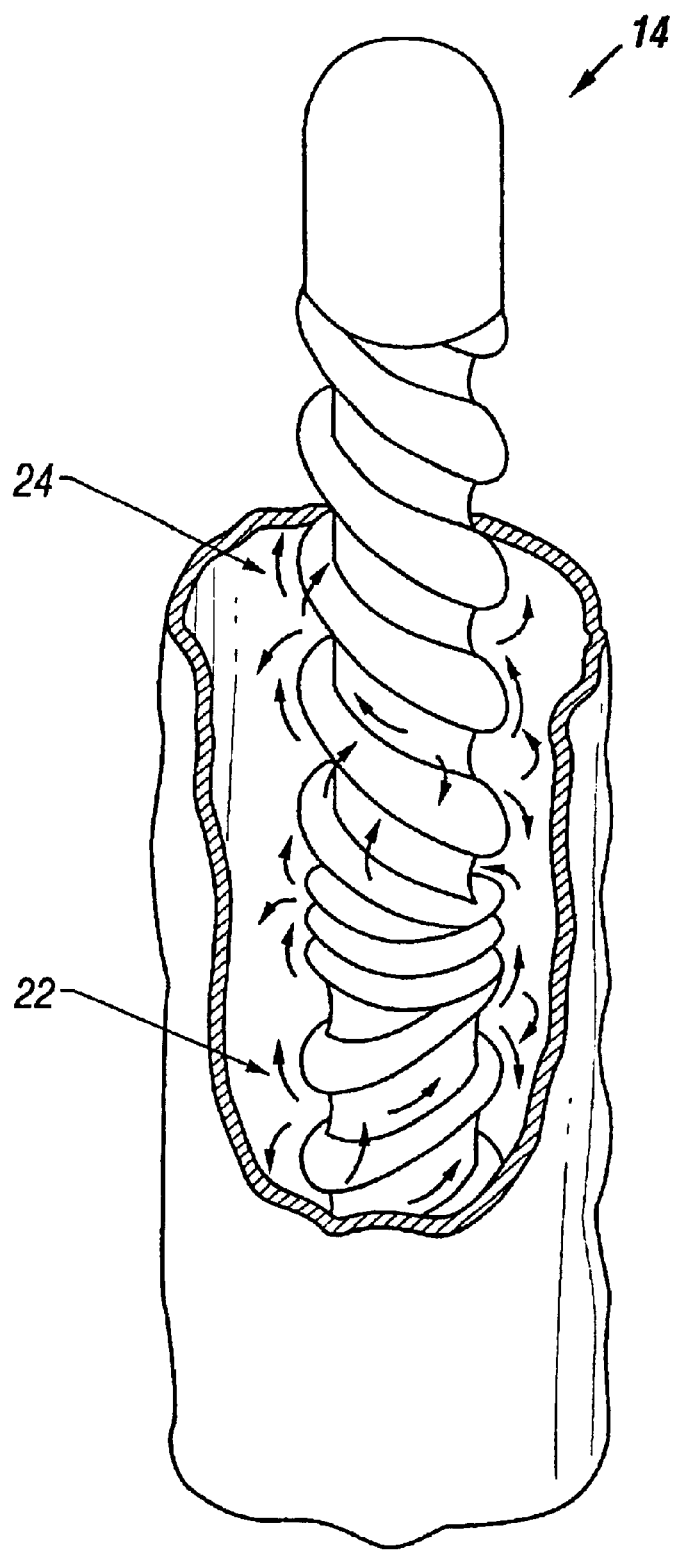
FIG. 5 is a perspective view of the heat transfer element of FIG. 2 in use within a blood vessel.

FIG. 5 is a perspective view of a heat transfer element 14 in use within a blood vessel, showing only one helical lobe per segment for purposes of clarity. Beginning from the proximal end of the heat transfer element (not shown in FIG. 5), as the blood moves forward during the systolic pulse, the first helical heat transfer segment 20 induces a counter-clockwise rotational inertia to the blood. As the blood reaches the second segment 22, the rotational direction of the inertia is reversed, causing turbulence within the blood. Further, as the blood reaches the third segment 24, the rotational direction of the inertia is again reversed. The sudden changes in flow direction actively reorient and randomize the velocity vectors, thus ensuring turbulence throughout the bloodstream. During turbulent flow, the velocity vectors of the blood become more random and, in some cases, become perpendicular to the axis of the artery. In addition, as the velocity of the blood within the artery decreases and reverses direction during the cardiac cycle, additional turbulence is induced and turbulent motion is sustained throughout the duration of each pulse through the same mechanisms described above.

Thus, a large portion of the volume of warm blood in the vessel is actively brought in contact with the heat transfer element 14, where it can be cooled by direct contact rather than being cooled largely by conduction through adjacent laminar layers of blood. As noted above, the depth of the grooves 26, 30, 34 (FIG. 2) is greater than the depth of the boundary layer which would develop if a straight-walled heat transfer element were introduced into the blood stream. In this way, free stream turbulence is induced. In the preferred embodiment, in order to create the desired level of turbulence in the entire blood stream during the whole cardiac cycle, the heat transfer element 14 creates a turbulence intensity greater than about 0.05. The turbulence intensity may be greater than 0.05, 0.06, 0.07 or up to 0.10 or 0.20 or greater.

Referring back to FIG. 2, the heat transfer element 14 has been designed to address all of the design criteria discussed above. First, the heat transfer element 14 is flexible and is made of a highly conductive material. The flexibility is provided by a segmental distribution of bellows sections 25, 27 which provide an articulating mechanism. Bellows have a known convoluted design which provides flexibility. Second, the exterior surface area 37 has been increased through the use of helical ridges 28, 32, 36 and helical grooves 26, 30, 34. The ridges also allow the heat transfer element 14 to maintain a relatively atraumatic profile, thereby minimizing the possibility of damage to the vessel wall. Third, the heat transfer element 14 has been designed to promote turbulent kinetic energy both internally and externally. The modular or segmental design allows the direction of the invaginations to be reversed between segments. The alternating helical rotations create an alternating flow that results in mixing the blood in a manner analogous to the mixing action created by the rotor of a washing machine that switches directions back and forth. This mixing action is intended to promote high level turbulent kinetic energy to enhance the heat transfer rate. The alternating helical design also causes beneficial mixing, or turbulent kinetic energy, of the working fluid flowing internally.

Figure 6:
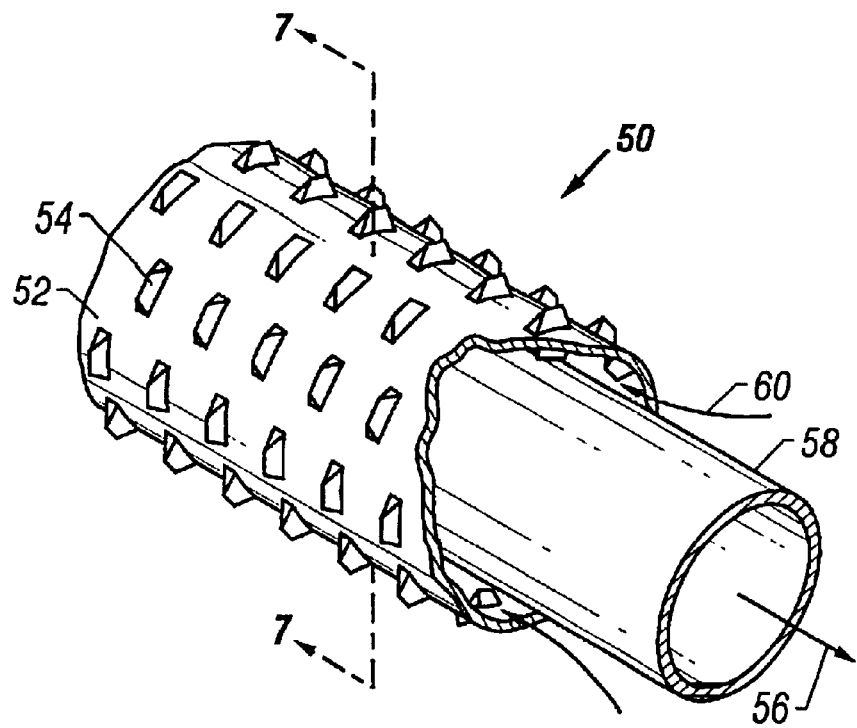
FIG. 6 is a cut-away perspective view of an alternative embodiment of a heat transfer element which may be employed according to the invention.

FIG. 6 is a cut-away perspective view of an alternative embodiment of a heat transfer element 50. An external surface 52 of the heat transfer element 50 is covered with a series of axially staggered protrusions 54. The staggered nature of the outer protrusions 54 is readily seen with reference to FIG. 7 which is a transverse crosssectional view taken at a location denoted by the line 7—7 in FIG. 6. In order to induce free stream turbulence, the height, $d_p$, of the staggered outer protrusions 54 is greater than the thickness of the boundary layer which would develop if a smooth heat transfer element had been introduced into the blood stream. As the blood flows along the external surface 52, it collides with one of the staggered protrusions 54 and a turbulent wake flow is created behind the protrusion. As the blood divides and swirls along side of the first staggered protrusion 54, its turbulent wake encounters another staggered protrusion 54 within its path preventing the re-lamination of the flow and creating yet more turbulence. In this way, the velocity vectors are randomized and turbulence is created not only in the boundary layer but throughout the free stream. As is the case with the preferred embodiment, this geometry also induces a turbulent effect on the internal coolant flow.

Figure 7:
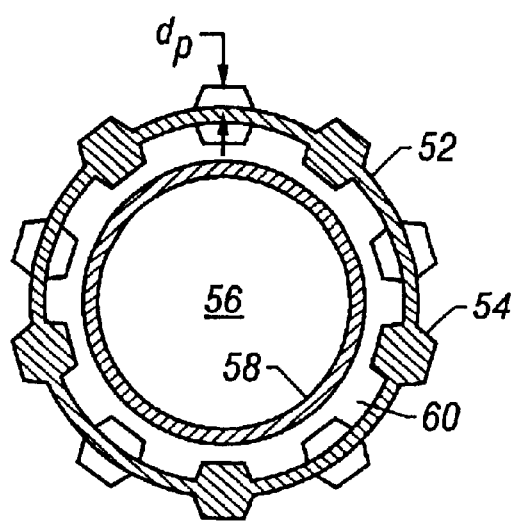
FIG. 7 is a transverse section view of the heat transfer element of FIG. 6.

A working fluid is circulated up through an inner coaxial lumen 56 defined by an insulating coaxial tube 58 to a distal tip of the heat transfer element 50. The working fluid then traverses an outer coaxial lumen 60 in order to transfer heat to the exterior surface 52 of the heat transfer element 50. The inside surface of the heat transfer element 50 is similar to the exterior surface 52, in order to induce turbulent flow of the working fluid. The inner protrusions can be aligned with the outer protrusions 54, as shown in FIG. 7, or they can be offset from the outer protrusions 54, as shown in FIG. 6.

Figure 8:
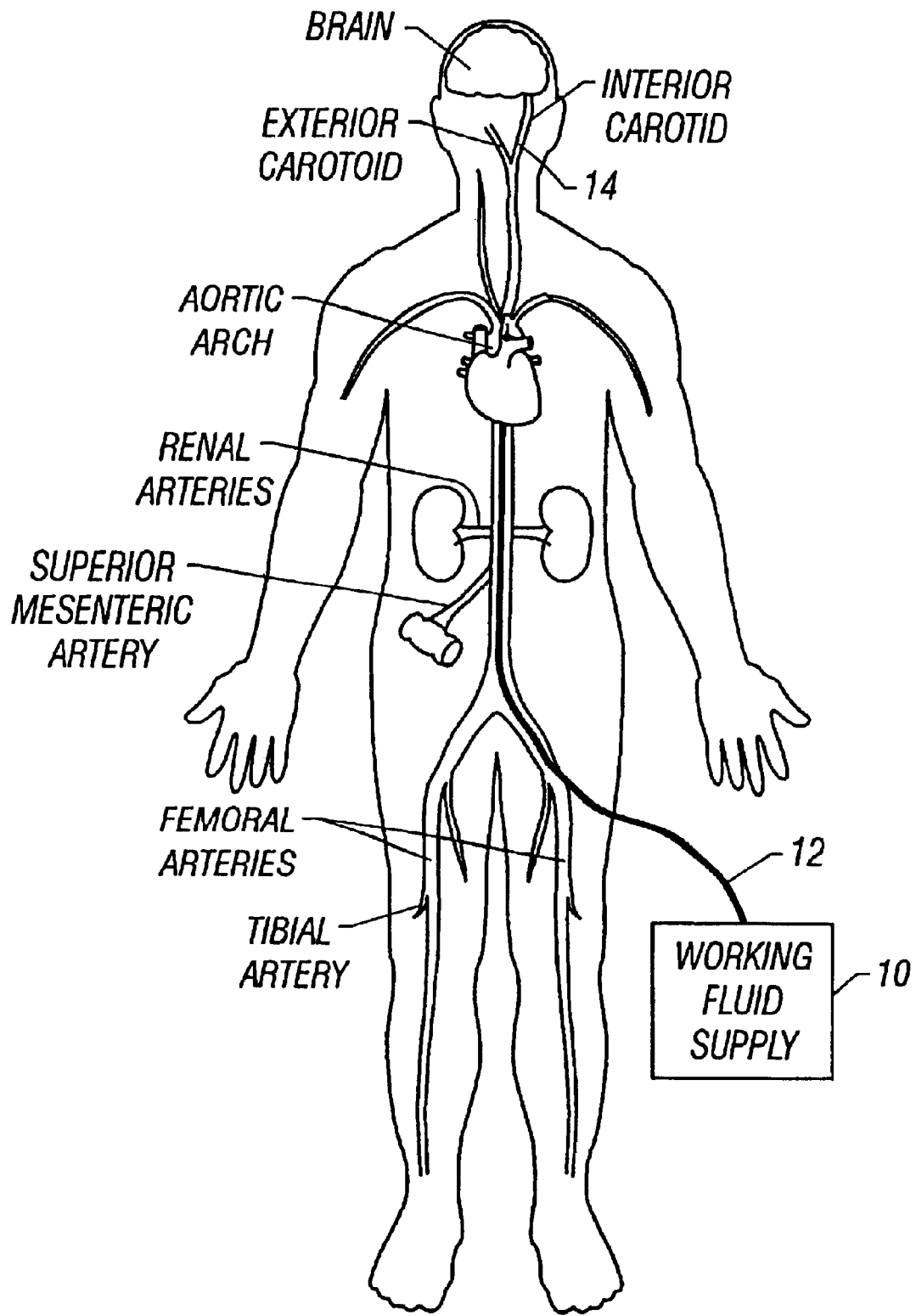
FIG. 8 is a schematic representation of the invention being used in one embodiment to cool the brain of a patient.

FIG. 8 is a schematic representation of the invention being used to cool the brain of a patient. The selective organ hypothermia apparatus shown in FIG. 8 includes a working fluid supply 10, preferably supplying a chilled liquid such as water, alcohol or a halogenated hydrocarbon, a supply catheter 12 and the heat transfer element 14. The supply catheter 12 has a coaxial construction. An inner coaxial lumen within the supply catheter 12 receives coolant from the working fluid supply 10. The coolant travels the length of the supply catheter 12 to the heat transfer element 14 which serves as the cooling tip of the catheter. At the distal end of the heat transfer element 14, the coolant exits the insulated interior lumen and traverses the length of the heat transfer element 14 in order to decrease the temperature of the heat transfer element 14. The coolant then traverses an outer lumen of the supply catheter 12 so that it may be disposed of or recirculated. The supply catheter 12 is a flexible catheter having a diameter sufficiently small to allow its distal end to be inserted percutaneously into an accessible artery such as the femoral artery of a patient as shown in FIG. 8. The supply catheter 12 is sufficiently long to allow the heat transfer element 14 at the distal end of the supply catheter 12 to be passed through the vascular system of the patient and placed in the internal carotid artery or other small artery. The method of inserting the catheter into the patient and routing the heat transfer element 14 into a selected artery is well known in the art.

Although the working fluid supply 10 is shown as an exemplary cooling device, other devices and working fluids may be used. For example, in order to provide cooling, freon, perflourocarbon, water, or saline may be used, as well as other such coolants.

The heat transfer element can absorb or provide over 75 Watts of heat to the blood stream and may absorb or provide as much as 100 Watts, 150 Watts, 170 Watts or more. For example, a heat transfer element with a diameter of 4 mm and a length of approximately 10 cm using ordinary saline solution chilled so that the surface temperature of the heat transfer element is approximately 5° C. and pressurized at 2 atmospheres can absorb about 100 Watts of energy from the bloodstream. Smaller geometry heat transfer elements may be developed for use with smaller organs which provide 60 Watts, 50 Watts, 25 Watts or less of heat transfer.

The practice of the present invention is illustrated in the following non-limiting example.

Exemplary Procedure

1. The patient is initially assessed, resuscitated, and stabilized.
2. The procedure is carried out in an angiography suite or surgical suite equipped with flouroscopy.
3. Because the catheter is placed into the common carotid artery, it is important to determine the presence of stenotic atheromatous lesions. A carotid duplex (doppler/ultrasound) scan can quickly and non-invasively make this determinations. The ideal location for placement of the catheter is in the left carotid so this may be scanned first. If disease is present, then the right carotid artery can be assessed. This test can be used to detect the presence of proximal common carotid lesions by observing the slope of the systolic upstroke and the shape of the pulsation. Although these lesions are rare, they could inhibit the placement of the catheter. Examination of the peak blood flow velocities in the internal carotid can determine the presence of internal carotid artery lesions. Although the catheter is placed proximally to such lesions, the catheter may exacerbate the compromised blood flow created by these lesions. Peak systolic velocities greater that 130 cm/sec and peak diastolic velocities greater than about 100 cm/sec in the internal indicate the presence of at least 70% stenosis. Stenosis of 70% or more may warrant the placement of a stent to open up the internal artery diameter.
4. The ultrasound can also be used to determine the vessel diameter and the blood flow and the catheter with the appropriately sized heat transfer element could be selected.
5. After assessment of the arteries, the patients inguinal region is sterilely prepped and infiltrated with lidocaine.
6. The femoral artery is cannulated and a guide wire may be inserted to the desired carotid artery. Placement of the guide wire is confirmed with flouroscopy.
7. An angiographic catheter can be fed over the wire and contrast media injected into the artery to further to assess the anatomy of the carotid.
8. Alternatively, the femoral artery is cannulated and a 10–12.5 french (f) introducer sheath is placed.
9. A guide catheter is placed into the desired common carotid artery. If a guiding catheter is placed, it can be used to deliver contrast media directly to further assess carotid anatomy.
10. A 10 f–12 f (3.3–4.0 mm) (approximate) cooling catheter is subsequently filled with saline and all air bubbles are removed.
11. The cooling catheter is placed into the carotid artery via the guiding catheter or over the guidewire. Placement is confirmed with flouroscopy.
12. Alternatively, the cooling catheter tip is shaped (angled or curved approximately 45 degrees), and the cooling catheter shaft has sufficient pushability and torqueability to be placed in the carotid without the aid of a guide wire or guide catheter.
13. The cooling catheter is connected to a pump circuit also filled with saline and free from air bubbles. The pump circuit has a heat exchange section that is immersed into a water bath and tubing that is connected to a peristaltic pump. The water bath is chilled to approximately 020 C.
14. Cooling is initiated by starting the pump mechanism. The saline within the cooling catheter is circulated at 5 cc/sec. The saline travels through the heat exchanger in the chilled water bath and is cooled to approximately 1° C.
15. It subsequently enters the cooling catheter where it is delivered to the heat transfer element. The saline is warmed to approximately 5–7° C. as it travels along the inner lumen of the catheter shaft to the end of the heat transfer element.
16. The saline then flows back through the heat transfer element in contact with the inner metallic surface. The saline is further warmed in the heat transfer element to 12–15° C., and in the process, heat is absorbed from the blood, cooling the blood to 30° C. to 32° C.
17. The chilled blood then goes on to chill the brain. It is estimated that 15–30 minutes will be required to cool the brain to 30 to 32° C.
18. The warmed saline travels back down the outer lumen of the catheter shaft and back to the chilled water bath where it is cooled to 1° C.

19. The pressure drops along the length of the circuit are estimated to be 2–3 atmospheres.
20. The cooling can be adjusted by increasing or decreasing the flow rate of the saline. Monitoring of the temperature drop of the saline along the heat transfer element will allow the flow to be adjusted to maintain the desired cooling effect.
21. The catheter is left in place to provide cooling for 12 to 24 hours.
22. If desired, warm saline can be circulated to promote warming of the brain at the end of the therapeutic cooling period.

The above devices and techniques, including those disclosed in the applications incorporated by reference above, provide effective cooling or heating of a fluid such as blood. The heating or cooling may occur either in the affected vessel or in a vessel in fluid communication with the affected vessel. In this disclosure, "fluid communication" between two vessels refers to a situation where one vessel either feeds or is fed by the other. One application of these devices and techniques is for clot lysis. However, other types of enzyme activations may also be advantageously induced. The method disclosed below is applicable to other devices and techniques so long as they are also capable of heating or cooling blood.

As noted above, enzymes have been delivered to patients in drug or intravenous form for clot lysing. These enzymes are in addition to naturally occurring enzymes already in the blood plasma. The activity of enzymes is at least partially adjusted by control of environmental temperature. A method according to an embodiment of the invention selectively controls enzyme activity by controlling the temperature of the environment of the enzyme. This controlled enzyme activity allows selective thrombolysis by selective vessel hypothermia in a manner described in more detail below.

Several experimental procedures have been reported on animals and clot preparations at various temperatures, as disclosed below, and appropriate temperature regimes for thrombolysis may be inferred with some accuracy. However, the mechanisms by which enzyme environmental temperature controls thrombolysis are not yet well characterized. Disclosed below are several suggested mechanisms. These suggested mechanisms are conjecture, and should not be construed as limiting, in any way, the method of the invention.

The suggested mechanisms rely to a certain extent on the known mechanisms for fibrinolysis. In particular, plasminogen is the inert precursor of plasmin. Plasmin is an enzyme that lyses clots, i.e., cleaves peptide bonds in fibrin. Plasminogen binds to fibrin and, when activated by an appropriate enzyme, such as tPA, UK, SK, etc., converts to plasmin. Plasminogen may also be activated in solution. Inhibitors such as $\alpha_2$-antiplasmin moderate plasmin activity by inactivating plasmin released from a fibrin surface almost instantaneously. $\alpha_2$-antiplasmin can even inactivate plasmin bound to a fibrin surface, but this process requires about 10 seconds.

One suggested mechanism concerns the action of the inhibitors. The activity of $\alpha_2$-antiplasmin is lessened at low temperatures and thus is less effective at inactivating plasmin. In this case, more plasmin is available to lyse clots and thus fibrinolysis is enhanced.

A related effect is due to the effect of plasmin levels on plasminogen levels. Increased plasmin levels may lead to increased plasminogen levels circulating in solution. Moreover, decreased activity of $\alpha_2$-antiplasmin also leads to increased plasminogen levels because $\alpha_2$-antiplasmin binds plasminogen, and less $\alpha_2$-antiplasmin means less of such binding.

Increased plasminogen levels also suggests several other mechanisms for clot lysing.

For example, plasmin cleaves single-chain urokinase ("scu-PA" or "pro-UK") to form UK, i.e., pro-UK is a precursor to UK. Pro-UK, like tPA, cannot efficiently activate plasminogen in solution, but it can readily activate plasminogen bound to fibrin. Thus, increased plasminogen, together with the body's own UK or tPA, or similar enzymes provided intravenously, may result in more localized lysing of fibrin, e.g., directly at the clot situs.

Another suggested mechanism results from increased plasminogen. UK can activate both plasminogen in solution and plasminogen bound to fibrin. Thus, increased plasminogen levels, together with the body's own UK, or that provided intravenously, results in both localized lysing of fibrin and enhanced activation of plasminogen in solution.

Another suggested mechanism results from the conjectured bond of plasmin to fibrin. Plasmin may stay bound to fibrin for a longer period in the hypothermic state. Thus, more time may be available to lyse clots, increasing overall fibrinolysis.

The hypothermic temperatures at which increased fibrinolysis occurs have not been fully explored. However, it has been shown that clot samples have benefited from temperatures of, e.g., 25° C. or below. For human patients, it is believed that temperatures of 30° C. to 32° C. may well be appropriate and advantageously employed in the method of the invention.

In a related embodiment of the invention, the method may further employ a step of rewarming the cooled organ from the low temperature of, e.g., 30° C. The temperature range for rewarming may be from about 20° C. to 37° C. depending on the patient, the condition, the hypothermic temperature, and so on. Rewarming has been shown to have a beneficial effect in certain studies, perhaps by increasing the rate at which clot lysis occurs. In another related embodiment of the invention, the method may further employ temperature cycling the blood in the vessel from a hypothermic temperature to a rewarmed temperature. In this way, the rewarming temperature regime is achieved repeatedly and thus so is the enhanced fibrinolysis.

EXAMPLE ONE (Non-drug)

Researchers have studied the effect of temperature on fibrinolysis in the context of drug studies. As part of these studies, control groups are investigated in which no drugs are introduced. In one such investigation using clot samples, clot lysis was investigated while varying clot temperatures in a range of 25° C. to 41° C. In the absence of drugs, enhanced clot lysis was seen at the lower part of the temperature range. It is believed that this study can be extended to humans, and thus fibrinolytic activity can be enhanced at lower temperatures.

EXAMPLE TWO (Non-drug)

In another non-drug study of the effect of temperature on fibrinolysis, clot lysis in dogs was investigated while varying clot temperatures in a range of 20° C. to 36° C. The dog's temperature was lowered from a normal temperature to a low temperature. A gradual rewarming period followed the low temperature period.

Enhanced clot lysis was observed at lower temperatures as compared to higher temperatures. In particular, the maximum fibrinolytic activity occurred in the early rewarming period, i.e., from 20° C. to about 25° C. It is believed that this study can be extended to humans, and that fibrinolytic activity can be enhanced at lower temperatures, especially during periods of rewarming.

An advantage of all of these embodiments of the method is that clot lysis can be achieved in a simple manner and without the need for drugs. An additional advantage results from the reduced temperature of the blood which helps to protect the cells from ischemia at the same time lysis is occurring. Thus, clot lysis and cooling occur simultaneously, providing an effective and aggressive dual therapy. When dual therapies are employed, cooling catheters may be inserted in both femoral arteries for transit to the brain. One cooling catheter cools the brain, while the other cools the blood in the artery leading to the clot. The latter provides the beneficial effects noted above.

In some cases, of course, the nature or extent of the clot is such that lysing may only occur with drug intervention. In these cases, thrombolytic drugs, such as those disclosed above, may be introduced to induce the fibrinolysis.

These drugs are effective at treating the thrombus. However, it may also be advantageous to cool the brain as a separate neuroprotective measure. The effectiveness of both therapies is enhanced when applied as soon as possible. Thus, it is often desirable to apply both therapies simultaneously. In this way, hypothermia is induced as a neuroprotective measure, and may further induce clot lysing per se in the manner described above.

A difficulty with this approach is that the techniques are interdependent. Drugs depend on enzymes for their activity, and enzymes are temperature-dependent. In fact, past studies have demonstrated that the enzyme activity of these specific thrombolytic drugs on clot samples is temperature-dependent. In other words, their effect on clot or thrombus lysis varies over a temperature range. For typical temperature-specific enzymes, the greatest activity occurs at an optimal temperature. The optimal temperature may be about 37° C. in the case of known thrombolytics, as this is the normal human body temperature.

Enzyme activity drastically reduces above certain temperatures as the enzyme denatures and becomes inactive. At the opposite extreme, enzyme activity reduces below certain temperatures as the enzyme lacks the energy necessary to couple to a substrate. Therefore, when the brain or other tissue is at a temperature different from normal body temperature, e.g., during hypothermia, an isoform of the enzyme is preferably used which has an optimal working temperature at the hypothermic body temperature. In this disclosure, such an isoform which is effective at a different temperature is said to have a "working temperature" at the different temperature or within a range of different temperatures.

In this disclosure, the term "isoforn" of an enzyme is used as follows. If a first enzyme catalyzes a reaction at a first temperature, and a different enzyme catalyzes the same reaction at a second temperature, then the different enzyme is an "isoform" of the first enzyme within the meaning intended here.

For patients undergoing hypothermia, the physician may preferably use a low-temperature isoform; for patients whose temperatures have been raised, the physician may preferably use a high-temperature isoform. The form of the enzyme will preferably have an optimal activity curve at or near the desired temperature. Known enzymes are described below, followed by a methodology for choosing enzymes which are not yet known.

EXAMPLE THREE
(SK)

Researchers have investigated the effect of temperature on the fibrinolytic activity of an SK mixture. In one such effort, clots were treated with a mixture of plasminogen (2 mg) and SK (100 IU) in a total volume of 15 ml PBS. The temperature of the clots was raised from 24° C. to 37° C. These researchers found that heating enhanced the fibrinolytic activity. In other words, heating from a hypothermic temperature to normal body temperature increased clot lysing for clots treated with SK.

It is believed that such general trends may be extended to patients without lack of accuracy. Patients may be provided with a drug such as streptokinase and may undergo hypothermia using, e.g., one of the devices or methods described above. In particular, a cooling catheter may be placed in an artery supplying blood to a thrombosed vessel. The catheter may include a separate lumen through which the SK mixture may be delivered. A coolant or working fluid may be supplied to the cooling catheter, causing the same to cool and to cool the blood adjacent a heat transfer element located at a distal tip of the cooling catheter. This cooling step may include the step of inducing turbulence in the blood flowing through the vessel and/or in the working fluid. SK may be delivered through the separate drug delivery lumen. The patient may then be rewarmed as the SK is delivered. The rewarming step may be accomplished by passing a warm saline solution as the working fluid.

EXAMPLE FOUR
(tPA)

Researchers have also investigated the effect of temperature on the fibrinolytic activity of tPA. Clots were treated with 2.5 µg/ml tPA and incubated at various temperatures (e.g., 37° C., 25° C., 10° C., 0° C., and −8° C.). Plasminogen activation was relatively high at low temperatures (e.g., 0° C. or −8° C.) and was much less at higher temperatures. In other words, these researchers found that, for tPA, cooling to a hypothermic temperature from normal body temperature increased fibrinolytic activity.

As above, it is believed that such trends may be extended to patients without lack of accuracy. In this case, patients may be provided with tPA and may undergo hypothermia using an above device placed in an artery supplying blood to a thrombosed vessel. The catheter may include a separate lumen through which tPA may be delivered. A coolant or working fluid may be supplied to the cooling catheter, causing the catheter and the adjacent blood to cool. This cooling step may include the step of inducing turbulence in the blood flowing in the vessel and/or in the working fluid. tPA may be delivered through the separate drug delivery lumen. In this case, the patient may not be rewarmed until the drug delivery is complete, or until the thrombus is dissolved.

EXAMPLE FIVE
(tPA)

Researchers have further investigated the effect of temperature on the fibrinolytic activity of tPA. Clots were treated with tPA in concentrations of 0.3 µg/ml, 1.0 µg/ml, and 3.0 µg/ml and incubated at various temperatures from 24° C. to 40° C. The amount of clot lysis correlated with temperature at all concentrations. However, contrary to the results indicated in Example Four, the amount of clot lysis at lower temperatures was less than that at higher temperatures. It is conjectured that heating may have enhanced the activation of plasminogen by the tPA, and that such heating may have a similar effect in patients. This general enhancement has also been seen in UK and SK systems.

Further research is clearly necessary to determine the optimal procedure. In any case, an embodiment of the method of the invention may be employed to advantageously perform either heating or cooling in an improved way. To enhance the activation of plasminogen by tPA, a warm saline solution may be provided in a catheter of the type described above. The warm saline solution transfers heat to the blood at a heat transfer element. An appropriate temperature range for the warm saline solution at a point within the heat transfer element may be about 38° C. to 74° C.

EXAMPLE SIX
(UK)

Researchers have also investigated the effect of temperature on the fibrinolytic activity of UK. In one such effort, clots were treated with a mixture of UK at temperatures of 4° C. and 28° C. A certain amount of fibrinolytic activity was induced by the introduction of the UK to the clots. Heating to 28° C. caused a second phase of activation, resulting in complete conversion of all plasminogen to plasmin, and thus increased fibrinolytic activity. In other words, heating from a very low temperature (4° C.) to a hypothermic temperature (28° C.) increased clot lysing. As above, it is believed that such trends may be extended to patients. As may be noted, this Example may be analogous to that of Example Three because of the rewarming step; a similar procedure may be employed to perform the procedure on patients.

The above examples indicate how drugs may be combined with temperature-altering devices as, e.g. are disclosed above, to provide simultaneous cooling and thrombolysis. This combination provides a power dual therapy which may be advantageously employed to aggressively treat stroke and other similar body insults. When dual therapies are employed, a cooling catheter may be inserted in one femoral artery for transit to the brain for neural protection. Of course, a heating catheter would be employed if a temperature rise were desired. Another catheter may provide the drug delivery. Alternatively, the heating or cooling catheter may have disposed therein a lumen for drug delivery.

The above examples have used known drugs. However, for all of the above and for similar techniques, an appropriate isoform of an enzyme may be employed to allow enzymatic activity at temperatures other than normal body temperature. One way to choose appropriate isoforms for these enzymes is by searching for the same in cold climates. For example, SK is a bacterial enzyme. Bacteria live in many different temperature environments. It is common to find or select an enzyme for a certain process or temperature by finding bacteria that live in environments having the desired temperature.

As another example, the polymerase chain reaction is a polynucleotide amplification process that requires an enzyme capable of surviving high temperatures. These enzymes were located in bacteria living in hot springs and thermal vents on the sea floor. Therefore, it is likely that certain bacteria that live in room temperature environments or arctic-like environments will have enzymes similar to those desired, i.e., SK that can survive hypothermic environments.

tPA and UK, on the other hand, are recombinant forms of human enzymes. As such, tPA and UK could be genetically altered to maintain their activity at lower temperatures. For example, the protein backbone could be changed to yield higher tPA or UK activity at lower temperatures.

While the method of the invention has been described with respect to specific devices and techniques which may be used to cool blood, other techniques or devices may also be employed. The embodiments of the method of the invention may advantageously employ the turbulence inducing devices and techniques disclosed above to enhance the heat transfer and thus the heating or cooling of the blood.

Furthermore, the invention has been described predominantly with respect to a particular lysing system: the lysing of a blood clot in a blood vessel such as is caused by stroke or myocardial infarction. However, the methods of the invention can be equally applied to altering the activity of any enzyme relative to its activity at normal temperatures. Furthermore, the invention may be applied to cooling solids, such as volumes of tissue, rather than blood flows or static volumes of blood. Moreover, the invention can be applied to heating blood or tissue, especially when such heating advantageously enhances desired activity in a specific enzyme.

The invention has also been described with respect to certain drug therapies. It will be clear to one of skill in the art that various other drugs may be employed in the method of the invention, so long as they have characteristics similar to those described above. Accordingly, the invention is limited only by the scope of the appended claims.

What is claimed is:

1. A method for dissolving a blood clot, comprising:

introducing a catheter having a cooling element into a blood vessel in which a blood clot has formed and disposing the cooling element within the blood vessel such that blood flows past the cooling element to the blood clot;

cooling at least a portion of the volume of blood surrounding the blood clot; and inducing mixing in a free stream in the blood flowing over the catheter;

whereby inhibition of anti-clotting enzymes by the cooling is reduced.

2. The method of claim 1, wherein the mixing of said inducing mixing step is caused by the shape of said cooling element.

3. The method of claim 2, wherein the cooling element has a plurality of beat transfer segments.

4. The method of claim 3, wherein the plurality of heat transfer segments are comprised of helical ridges to induce mixing within the free stream in the blood flowing over the catheter.

5. The method of claim 1, wherein the cooling element is flexible.

* * * * *